United States Patent [19]

Smith et al.

[11] Patent Number: 5,328,450

[45] Date of Patent: Jul. 12, 1994

[54] ABSORBENT DEVICES AND PRECURSORS THEREFOR

[75] Inventors: Mark F. Smith, Sheering; Patrick L. Blott, Bishops Stortford, both of United Kingdom

[73] Assignee: Smith & Nephew plc, United Kingdom

[21] Appl. No.: 127,427

[22] Filed: Sep. 27, 1993

Related U.S. Application Data

[63] Continuation of Ser. No. 681,528, filed as PCT/GB90/00398, Mar. 16, 1991, abandoned.

[30] Foreign Application Priority Data

Mar. 16, 1989 [GB] United Kingdom ............. 8906100

[51] Int. Cl.⁵ .................. A61F 13/00; A61F 15/00; A61F 13/15; A61L 15/00
[52] U.S. Cl. ...................... 602/59; 602/41; 602/42; 602/43; 602/46; 602/47; 602/58; 604/304; 604/358; 604/366; 604/369; 604/370; 604/378; 428/138
[58] Field of Search .............. 428/131, 137, 138, 159, 428/160, 198; 602/41–43, 46–47, 52, 57–59; 604/304, 306–307, 358, 366–367, 369–370, 372, 378, 380, 382, 383, 385.1

[56] References Cited

U.S. PATENT DOCUMENTS

| | | | |
|---|---|---|---|
| 3,292,619 | 12/1966 | Egler | 128/156 |
| 3,949,742 | 4/1976 | Nowakowski | 128/156 |
| 4,541,426 | 9/1985 | Webster | 128/156 |
| 4,657,006 | 4/1987 | Rawlings et al. | 602/47 |
| 4,798,604 | 1/1989 | Carter | 604/370 |
| 4,846,813 | 7/1989 | Raley | 604/378 |

Primary Examiner—Randall L. Green
Assistant Examiner—P. Zuttarelli
Attorney, Agent, or Firm—Rosenman & Colin

[57] ABSTRACT

An absorbent device which comprises an absorbent layer having an apertured contoured polymer film attached to a surface, wherein this surface is provided with a plurality of depressions which communicate directly with the apertures in the film. The device may be produced by separating the polymer film and a carrier material which have been formed into a laminate having impressed therein raised areas defining, for example, the strands of net and depressed areas such that upon separation the depressed areas of the film remain attached together with associated portions of the attached absorbent, to the carrier, leaving the raised areas attached to the remainder of the absorbent.

20 Claims, 3 Drawing Sheets

ABSORBENT DEVICES AND PRECURSORS THEREFOR

This application is a continuation of application Ser. No. 07/681,528 filed as PCT/GB90/00398, Mar. 16, 1990 which is now abandoned.

FIELD OF INVENTION

The present invention relates to absorbent devices, to a laminate which is a precursor for an apertured and contoured film or net and to the film or net itself. The present invention also relates to processes for preparing absorbent devices, the laminate and apertured film or net formed therefrom, and to the use of the film or net as a body contacting layer in absorbent products such as dressings and hygienic devices.

BACKGROUND OF THE INVENTION

Absorbent devices such as dressings and hygienic devices conventionally employ a water permeable film for their body contacting surface to act as a barrier between the body surface and the absorbent. A wound contacting layer, for example, for use in a dressing should also be conformable, non-adherent to the wound and to act as a means of preventing the healing wound incorporating the absorbent material into regenerating surface. One successful non-adherent absorbent wound dressing comprises a hydrophilic polyurethane foam bonded to a wound contacting layer comprising an elastomeric separator layer which is the polymer net.

Those prior art dressings may be made by casting the net in a mold and then casting the foam on top of the net. This process involves many steps, expensive raw materials and imperfections in the mold may cause uneven net strand thickness and prevent clean release of the net from the mold. A further disadvantage is that the surface of the absorbent between the strands may be very close to the surface of the dressing hence presenting an opportunity for the absorbent to become incorporated in the healing wound or for the dressing to be more adherent than desirable under some circumstances.

SUMMARY OF THE INVENTION

The present invention accordingly provides an absorbent device comprising an absorbent layer and an apertured contoured polymer film attached to one surface which surface is provided with a plurality of depressions which communicate directly with the apertures in the film.

The absorbent device is preferably a wound dressing. It has been found that such dressings allow for excellent healing of the wound, do not adhere significantly and are easier to manufacture than prior art dressings.

The apertured contoured polymer film is a three-dimensional structure whose major surfaces are in spaced apart planes. The major surfaces of this structure are defined respectively by one surface of the raised portions of the contoured film and by the opposed surface of depressed portions of the film. The apertures in the film preferably all lie in the plane defining one of the major surfaces of the-film and it is to this surface that the second layer is attached to the first layer. The apertures in the second layer register with voids formed by the depressions in the surface of the absorbent layer but the film material does not normally extend significantly into the voids.

The apertures in the film may be of a size and shape to give the apertured film the appearance of a net. For example, if the apertures are quadralaterals, the non-apertured part of the film will resemble the strands and junctures of a net. Circular or other non-rectilinear apertures may give the apertured film a different appearance. The apertured contoured film is preferably a net having strands and junctures formed from the polymer material.

A process has also now been found which makes the task of preparing a net or apertured contoured film suitable for use, for example, as a wound contacting layer cheaper and simpler. The separator layers when used in dressings have been found to possess advantages over the separator layers previously used. These advantages occur as a result of the process used for their manufacture. The second or separator layer employed in the absorbent devices of the invention may be formed by laminating together a carrier material and a film which is to form the apertured or contoured film under conditions such that the laminate possesses an impressed pattern of raised areas, e.g., defining the strands of a net. Between these areas or strands are defined membrane areas which are depressed areas in the film. Separation of the film from its carrier again by peeling them apart results in the membrane areas of the film remaining adhered to the carrier material and the intersecting strands remaining, form the net. The laminate possessing these properties is novel. The production of the net via the laminate is simple, quick and not wasteful of raw materials.

The present invention also provides a laminate having impressed therein a pattern of raised areas with depressed areas therebetween, said laminate comprising a carrier material and a film, wherein said film and material are attached to each other such as to permit, upon separation, the membrane areas of the film to remain attached to the carrier material.

In another aspect, the present invention provides a contoured apertured film which has been produced by the separation of a contoured polymer film and a carrier material which have been formed into a laminate having impressed therein a pattern of raised areas of the net and depressed areas, said film and carrier material being attached to each other such that upon separation thereof the depressed areas of the contoured film remain attached to the carrier material.

In a preferred embodiment of the invention the laminate is impressed with a pattern of raised areas which will define the intersecting strands of a net. The depressed areas define a membrane between the strands and upon separation of the carrier from the contoured film the membrane areas rupture to form the apertures of the net and the remaining, raised areas define the intersecting strands of the net.

A major advantage has been recognized in the preparation of dressings in which the net is adhered to an absorbent material. The absorbent material such as a foam may be cast onto the contoured film of the laminate before separation of the film and its carrier. In this method there is no risk of the foam exuding through the openings in the film since the film is not yet apertured. Separation of the carrier material from the foam coated film now not only removes the membrane areas but will also remove a little of the foam from between the strands which has adhered to the membrane areas. This results in deeper depressions in the foam surface between the strands so reducing the risk of the foam surface ever contacting the healing wound and also makes more surface of the foam available from absorbing body fluids.

The carrier material can be any deformable material. Aptly it can be a plastics film and preferably can be a thermoplastic film in which the polymer which forms the film can have a melting point above that of the polymer forming the contoured film. Suitable films include pololefin and polyester films, for example low density polyethylene or a polyester film, available as Melinex (Trade mark) and polyamide materials such as Nylon films. Other deformable materials which are suitable include cellulosic products such as PVdC laquered cellulose and nitocellulose coated cellulose and uncoated products such as those sold under the trade name Cellophane and paper. The carrier material may be of any desirable thickness provided that, when laminated to the net-forming film, it is capable of being embossed and retaining the debossant. Aptly the carrier material will be at least 30 µm thick. The thickness of the carrier material can be from 50 to 250 µm, more suitably can be 100 to 175 µm and is preferably 125 to 150 µm.

The material for forming the apertured contoured film can be a polymer which flows under the influence of pressure and/or heat.

Aptly the film comprises an elastomer and preferably a thermoplastic elastomer.

Apt materials for use in forming the apertured contoured film include di- and tri-block copolymers such as those of hard block materials such as styrene with softer block elastomeric materials such as isoprene or butadiene. Suitable materials in this group include block copolymer sold under the trade names KRATON TM and CARIFLEX TM.

Other apt elastomers for use in forming the apertured contoured film include hydrocarbons such as polyethylene or polyisobutadiene, polyester ether, polyester amides, polyurethanes and other copolymers such as ethylene-vinyl acetate copolymers or mixtures of such elastomers.

Suitable polyether-amide elastomers are disclosed in British Patent 1473972, French Patent Nos. 1444437 and 2178205 and U.S. Pat. No. 3,839,245. An apt polyether-amide is known as Pebax 2533 SN00 available from ATO Chemical Products (U.K.) Limited. This polymer has a water content of approximately 55% when hydrated.

Suitable polyether-ester elastomers for use in the invention are known as Hytrel available from Du Pont (U.K.) Limited. An apt grade is known as Hytrel 4036.

Suitable polyurethane elastomers for use in the films used in the invention include relatively non-hydrophilic linear polyester polyurethanes and linear polyether polyurethane elastomers for example those known as Estanes available from BF Goodrich (U.K.) Limited. Apt grades are Estanes 5701, 5702, 5714 and 58201.

Hydrophilic polyurethane elastomers, for use in the invention, can aptly have a water content when hydrated of at least 5% by weight. Suitably such elastomer may absorb upto 70% by weight, desirably from 10% to 40% by weight and preferably from 20% to 30% by weight, for example 25% by weight, water when hydrated. Suitable hydrophilic linear polyurethane elastomers for use in the invention are described in United Kingdom Patent No. 2093190.

Other suitable elastomeric acrylic polymers such as a copolymer of alkoxy alkyl acrylate or methacrylates, as for example those described in United Kingdom Patent Sepcification No. 1280631 and ethylene-acrylic acid or acrylic ester polymers such as those sold under the trade name PRIMACOR TM and LOTADUR TM.

Preferably the material for forming the apertured contoured film is a blend, suitably a blend of an elastomeric material with an incompatible more rigid polymeric material. Such blends may comprise the above described elastomeric materials with a polyolefin such as polyethylene, polystyrene polycyclooctene or polypropylene.

Suitable blends include those of ethylene-vinyl acetate copolymers, polyurethane or polybutadiene with an incompatible polymers such as a polyolefin, for example polystyrene. Such blends are described for example in European Patent Specification Nos. 0141542 and 0046071 and in United Kingdom Patent Specification No. 2103537. Other preferred blends include those polyether-amides with high impact polystyrene, non-hydrophilic polyurethanes with hydrophilic polyurethanes, and polyurethane with linear low density polyethylene.

The ratio of elastomeric material to the other blend components is desirably chosen so that the elastomeric materials form the continuous phase of the blend and the other materials are in the discrete or discontinuous phase. Generally the elastomeric components will form at least 50% by weight of the blend. Aptly the blend will contain upto 90% by weight of the elastomeric components. Suitably the blend will contain between 55 and 85% of the elastomeric components. Certain ethylene polymers such as low density polyethylene and linear low density polyethylene exhibit some elastic properties therefore may be considered to be part of the elastomeric components of blends containing such materials.

Preferred blends of an ethylene-vinyl acetate copolymer comprise from 10% to 90% by weight of ethylene-vinyl acetate copolymer more preferably 20 to 80% by weight of ethylene-vinyl acetate copolymer. Typical examples of such a blend comprises a blend of 40 parts ethylene-vinyl acetate copolymer and 60 parts high impact polystyrene, or a blend of about 25 parts ethylene-vinyl acetate copolymer, about 13 parts high impact polystyrene and about 60 parts linear low density polyethylene or a blend of from 40 to 90 parts by weight of ethylene-vinyl acetate copolymer and 60 to 10 parts by weight of high impact polystyrene.

The thickness of the film can be up to 250 µm, suitably from 25 to 200 µm, more suitably can be up to 150 to 175 µm and is preferably from 30, more preferably from 60 to 150 µm.

The films for forming the second layer may include filler materials or whitening agents such as calcium carbonate, titanium dioxide and the like. A suitable filled film is a polyethylene containing calcium carbonate.

The laminate can have membrane areas of any shape that can be produced by embossing. Such areas may be circular, elipsoidal, polygonal such as hexagonal or of more complex shape such as lobate, e.g., trifoliate shape. Preferably the membrane areas are, quadralateral e.g., diamond shaped or rectangular, for example, they may be square. The membrane areas can have dimensions of from 0.02 to 4 mm, more suitably can be from 0.05 to 2.5 mm and preferably from 0.1 to 2 mm. These dimensions are based on the side of a rectangle, other shaped areas will have areas and dimensions corresponding to major axes of the shape.

The depressed or membrane area can form at least 15% of the surface area of the laminate. Suitably the membrane area will form up to 80%, more suitably from 25 to 75% and preferably from 25 to 65% of the surface area of the laminate.

The laminate can have depressed areas corresponding to from 2 to 40 strands per cm of film surface, more suitably can have 3 to 40 strands per cm and preferably can have 4 to 24 strands per cm in both longitudinal and transverse directions.

The thickness of the embossed film, i.e., distance between the planes of the major surfaces of the second layer can be from 0.1 mm to 0.5 mm and is preferably 0.15 to 0.4 mm.

When the film is removed from the carrier material the film fractures around the perimeter of the membrane area to form apertures. The apertures in the film are equivalent area to the membrane areas described above. The strands or depressed areas in the apertured film retain their three dimensional character that is retain an arch shaped profile.

The laminate can be prepared by leading the carrier material and the polymer film together through the nip of two rollers. The first roller is a hard steel roller coated with a smooth rubber such as Hypolon (Trade mark). Generally, this roller is not heated. The roller contacts the film. The second roller is a steel roller which has an embossed pattern in its surface. A preferred embossed pattern can be of individual truncated square pyramids with troughs between the base edges of the pyramids. This roller can be heated. The film and carrier are laminated as they pass between the plain roller. The film and carrier passing between the plain roller and raised areas of the embossed roller form the membrane areas. The film and carrier deform into troughs between the depressed areas to form the raised areas or strands. The film and carrier leave the nip as a laminate with an impressed pattern of strands with the membrane areas in between. The net or apertured film is formed by peeling apart the film and carrier. The film fractures around the laminated membranes so that the membrane areas of the net-forming film remain adhered to the carrier material and the intersecting strands form the net.

Thus, the adhesive strength between the carrier and the film in the membrane region has to be greater than that in the region of the strands or raised areas and the adhesive strength in the absorbent should be less than the adhesive strength between the carrier and the film in the membrane region.

The pattern of the impressed raised areas or strands and depressed areas or membranes can depend upon the pattern engraved on the surface of the roller. Unequal density of strands in either longitudinal or transverse directions may lead to rectangular holes in the net; likewise continuous parallel strands in one direction with staggered arrangement of strands in the other direction can lead to brickwork pattern; strands arranged at angles to each other can give a diamond pattern and different shaped embossments, for example circular or hexagonal can lead circular or hexagonal apertures respectively. The engraved surface can contain mixed patterns or may contain plain areas where no pattern is impressed or laminate is formed.

In another aspect therefore, the present invention provides a process for the preparation of a laminate having a pattern of raised areas defining strands with depressed areas therebetween defining membrane areas and comprising a carrier material and a polymer film which can be separated after lamination such that the membrane area of the film remains attached to the carrier material and the strands form a contoured apertured film net which process comprises laminating the films together between a plain and embossed surface under the influence of heat and/or pressure.

In another aspect, the present invention provides a process for the preparation of a contoured apertured film or net which comprises separating the film and its carrier forming the laminate described hereinbefore.

If the apertured contoured film or net is to form the wound contacting layer of an absorbent dressing in which an absorbent material is attached to the net, then it is advantageous to attach the absorbent to the film before this film is removed from the carrier material to form the apertured contoured film net. Removal of the carrier material provides an absorbent material having one surface attached to a net.

Accordingly in another aspect the present invention comprises a laminate as hereinbefore described which has additionally an absorbent material attached to the surface of the polymer film remote from the carrier material.

Suitably the surface of the polymer film to which the absorbent is to be attached may be treated to enhance bonding. Such treatments can include a corone-discharge treatment of the film or the application of a suitable adhesive thereto.

The absorbent material employed in the absorbent layer can be any one of those conventionally used in absorbent dressings including gauze, wood pulp, cotton webs, rayon fibres and foams especially hydrophilic foams. Preferably the absorbent material is a foam. More preferably the absorbent layer comprises a conformable, hydrophilic foam. Apt foams may be made from polyurethane, carboxylated butadiene-styrene rubber, polyacrylate, polyester foams, hydrophilic epoxy foams and hydrophilic polyurethane foams described in European Patent Application No. 299122 which are incorporated herein by cross-reference.

Favored hydrophilic polymer foams are formed from hydrophilic polyurethane, especially cross-linked hydrophilic polyurethane. Such hydrophilic polyurethanes will generally absorb at least 5% by weight of water when hydrated and aptly will absorb up to 300 or 400% of their weight of water when fully hydrated. Preferred foams include those described in European Patent Specification No. 299122 and known as Hypol foams made from Hypol hydrophilic isocyanate terminated prepolymers (Hypol is a trade mark and is available from W. R. Grace and Co). The prepolymers are mixed with water and coated onto the net-forming film of the laminate where foaming occurs. The foam is then cured. The carrier material may then be removed. Removal of the carrier material results in not only removal of the membrane areas of the film but also a small amount of foam attached to them. The recesses between the strands are noticeably deeper than observed previously which means that the absorbent surface is at greater distance from the wound surface and hence is less likely to become integrated with the healing wound.

Aptly the absorbent material can have a thickness of at least 0.5 mm and suitably will have a thickness up to to 20 mm. More suitably the absorbent will be 1 to 15 mm preferably 2 to 10 mm, for example 4 mm, 6 mm, or 8 mm. thick.

If the absorbent material is other than a foam an adhesive may be used to adhere the absorbent to the film or laminate. Removal of the carrier film removes the membrane areas and cause cohesive failure in the absorbent material so a little absorbent is removed from the area between the strands as before.

In yet another aspect, the present invention provides a process for the preparation of a foam-coated laminate, said laminate having impressed therein a pattern of raised areas defining intersecting strands having membrane areas defined therebetween and comprising a carrier material and a contoured polymer film which can be separated after lamination such that the membrane areas of the film remain attached to the carrier material and form apertures in the film which process comprises laminating a polymeric film and carrier therefore together between a plain and embossed surface under the influence of heat and/or pressure forming a foam on the surface of the laminate and curing the foam.

In another aspect, the present invention comprises a process for preparing a wound dressing which comprises separating the carrier material from the foam-coated laminate described hereinbefore.

The absorbent material can contain topically effective medicament. Most suitably the medicament is an antibacterial agent. Preferably the antibacterial agent is a broad spectrum antibacterial agent such as silver salt such as silver suphadiazine, an acceptable iodine source such as polyvinyl pyrrolidone-iodine, chlorhexidine salts such as digluconate, diacetate, dihydrochloride or the like or quaternary antibacterial agents such as benzalkonium chloride.

The medicament can be present in amounts of at least 0.2% by weight of the dressing, and aptly upto 20% by weight of the dressing. More suitably from 0.3 to 10% by weight and preferably 0.5 to 5% by weight of the dressing of medicament may be incorporated.

In another type of dressing, the surface of the foam may have continuous moisture vapor transmitting conformable film over the surface opposed to the attached to the contoured apertured film or net. This further film may be used to regulate the moisture loss from the wound area under the dressing and also to act as a bacterial barrier to prevent bacteria penetrating to the wound area.

The moisture vapor permeability of a film is expressed by its moisture transmission rate and can be determined as follows.

Discs of the material under test were clamped over Payne Permeability Cups (flanged metal cups) using sealing rings and screw clamps. The exposed surface area of the test sample is 10 cm$^2$. Each cup contains approximately 10 ml of distilled water.

After weighing the cups are placed in a fan assisted electric oven which is maintained at 37°±1° C. The relative humidity within the oven is maintained at 10% by placing 1 Kg of anhydrous 3-8 mesh calcium chloride on the floor of the oven.

The cups are removed after 24 hours, allowed to cool for 20 minutes and re-weighed. The moisture vapor transmission rate of the test material is calculated from the weight loss and expressed in units of grams of weight per square meter per 24 hours. The units for moisture vapor transmission rate will hereinafter be expressed as gsm.

Apt continuous films can have a moisture vapor transmission rate of greater than $300^{-2} 24 h^{-1}$ at 37° C. and 100% to 10% relative humidity difference. Suitably the moisture vapor transmission rate would not normally be greater than 5000 gm$^{-2}$ 24 h$^{-1}$ at 37° C. and 100% to 10% relative humidity difference. Preferably, the moisture vapor transmission rate will be greater than 500, more preferably at least 700 and most preferably at least 2000 gm$^{-2}$ 24 h$^{-1}$ at 37° C. and 100% to 10% relative humidity difference.

Suitable polymers for use as a continuous film include polyether or polyester polyurethane or blends of polyurethanes with incompatible polymers such as polyolefins, for example polystyrene and may include those materials described above for producing the contoured apertured film. Aptly the films will be at least 12.5 thick. Suitable films will be up to 50 μm thick, favorably between 25 and 40 μm thick.

Preferred polyurethane films are made from linear polyurethanes as hereinbefore described with respect to the wound facing layer. Favored continuous films will be 12.5 micron to 37.5 micron thick. A preferred polyurethane for use in such thickness is Estane 5714F. A 25 micron thick film of Estane 5714F has a moisture vapor transmission rate of approximately 1800 gsm so that it may be employed to produce a moisture vapor transmission within the preferred range.

The outer layer can be a conformable polyurethane incompatible polymer blend film containing voids.

Suitable conformable polyurethane blend films are disclosed in United Kingdom Patent Application No. 8214250, now published as Application No. 2081721.

Apt conformable polyurethane blend film outer layers have a thickness 0.0125 mm to 0.125 mm. Such films can have a moisture vapor transmission rate of at least 500 gsm and preferably at least 1000 gsm.

A preferred polyurethane blend film comprises a blend of a linear polyurethane (60 parts by weight of Estane 580201 available from B. F. Goodrich) and a high impact polystyrene (40 part by weight of compound ref. 6MW available from R. H. Cole Limited). A favoured film of this composition has a thickness of 0.084 mm and a moisture vapor transmission rate of 1660 g/m$^2$/24 hours at 37.5° C. at 100% to 10% relative humidity difference.

The continuous film can be applied by spraying a solution of the polymer forming the film onto the foam surface.

In other aspects the present invention provides a foam-coated laminate as hereinbefore described in which the foam layer is attached to a continuous moisture vapor permeable film and a low wound adherency dressing form from this laminate.

The invention also provides a process for making this laminate and the dressing made by said process.

The laminate which includes the absorbent layer may be made available as a dressing precursor with the hospital personnal preparing the dressing in situ tearing off the carrier material.

The wound dressing aspect of this invention may be in any convenient form though a dressing of generally rectangular or circular shape may be preferred.

Suitable sizes for rectangular pads are from 5 cm×5 cm to 30 cm×30 cm. An alternative form is the form of an elongate strip which may be in the form of a roll.

Aptly absorbent devices of the invention, including those having a continuous moisture vapor transmitting film over the absorbent layer will have a moisture vapor transmission rate of at least 300 gsm, preferably at least 500 gsm, more preferably more than 700 gsm. The upper limit will be dictated by the moisture vapor transmission rate of the continuous film, if present. Absorptive devices, for example those suitable for use as wound dressings will have moisture vapor transmission rates of not more than 5000 gsm more aptly not more than 3000 gsm and preferably not more than 2000 gsm.

It is desirable that the wound dressing aspects of this invention are sterile and are provided in bacteria impervious pouches. Such packaged forms may be prepared under aseptic conditions from sterile components or may be sterilized after packing by a conventional procedure such as heat sterilization or ethylene oxide or gamma irradiation.

The wound dressings of the present invention have improved adherency properties when compared with conventional foam-net dressings. We have observed that dressings in accordance with the invention may require only half the force required to remove a conventional foam-net dressing from equivalent wounds.

The absorbent devices of the invention may also be employed for use as first aid dressings. Additionally they may be employed as sanitary napkins and baby diapers.

DETAILED DESCRIPTION OF THE DRAWINGS

Figure 1:
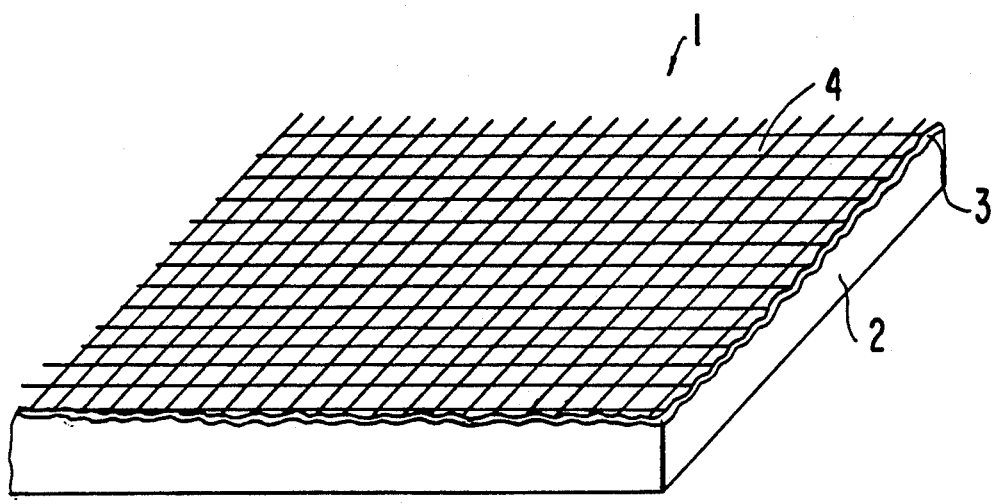
FIG. 1 is a view in perspective showing the absorbent device (1) of the invention wherein the absorbent layer (2) has a contoured polymer film (3) attached thereto, the contoured polymer film having a carrier material (4) attached to the side opposing the absorbent layer.
Figure 2:
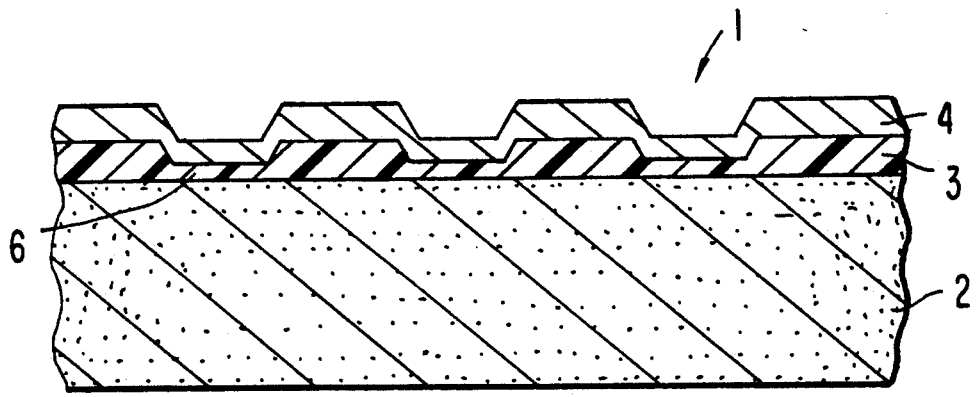
FIG. 2 is a view in a section of the absorbent device (1) shown in FIG. 1 wherein the laminate of the contoured polymer film (3) and the carrier material (4) has raised areas defining strands (5) and depressed areas defining membrane areas (6).
Figure 3:
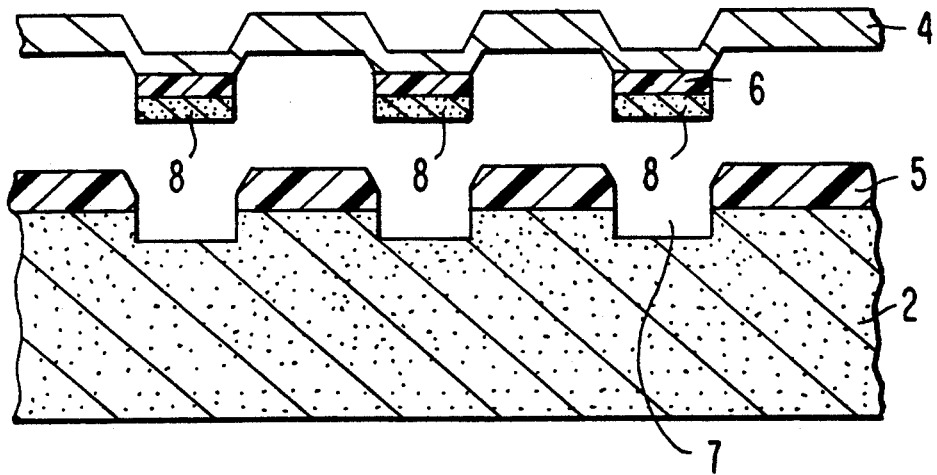

FIG. 3 is a view in a section of the carrier material (4) and absorbent layer (2) separated from one another. Carrier material (4) has membrane areas (6) attached thereto, the membrane areas having a small amount of foam (8) from the absorbent layer attached thereto. The absorbent layer (2) has recesses (7) between the strands (5).

Figure 4:
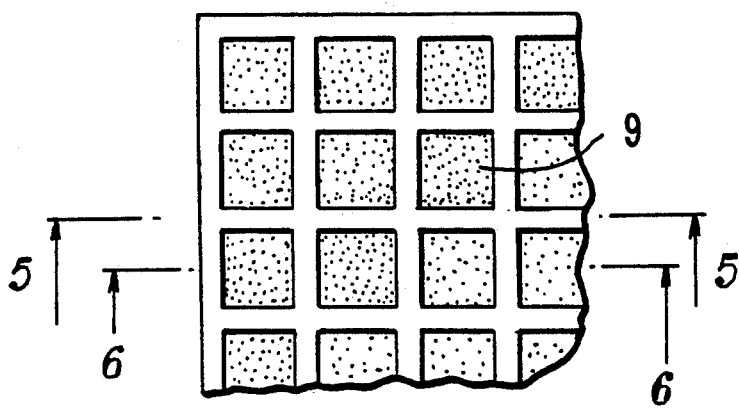

FIG. 4 is a planar view of the dressing of the invention with its carrier layer removed to reveal strands defining apertures (9) in the apertured contoured polymer film.

Figure 5:
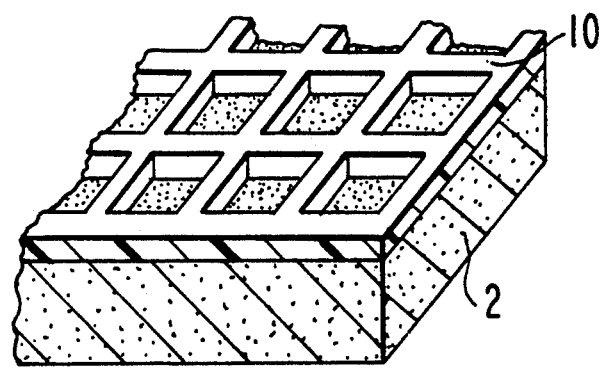

FIG. 5 is a perspective view in section through line A—A of FIG. 4 showing the apertured contoured polymer film (10) attached to the absorbent layer (2).

Figure 6:
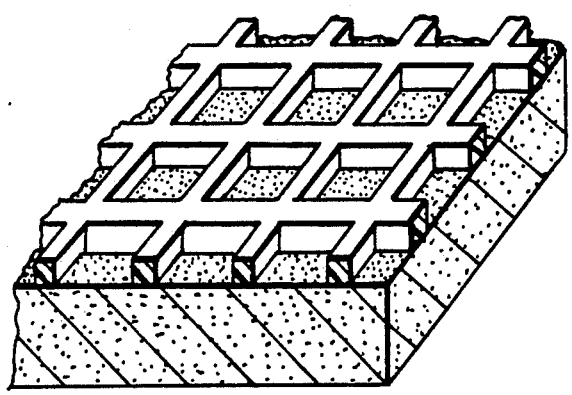

FIG. 6 is a perspective view in section through line B—B of FIG. 4 showing the apertured contoured polymer film attached to the absorbent layer.

EXAMPLE 1

A polymer blend containing 90 parts by weight of ethylene-vinyl acetate copolymer (containing 28% vinyl acetate) and 10 parts by weight of high impact polystyrene and 4% by weight of the polymers of titanium dioxide was formed by mixing the polymers in a heated blade mixer, forming into a sheet and then granulating. The granules were formed into a film of thickness 125 $\mu$m by extrusion through the nip of a two roller casting unit. The film was taken up to a roll. This was the net-forming film.

The polymer blend film and carrier of low density polyethylene, of thickness 150 $\mu$m, were lead, in contact between the nip of two rollers. The first roller comprises a hard rubber coated roller devoid of pattern and at room temperature. This roller was in direct contact with the polymer blend film. The second roller comprised a heated steel roller engraved with a pattern of raised discrete truncated square pyramids. The roller had a pattern of 4×4 raised areas per sq cm to truncated top of which had an area of 2×2 mm. This roller contacted the polyethylene film. The influence of the heat and pressure produced a laminate of the two films which had impressed into it the pattern on the roller. The pattern comprised intersecting strands defining square membrane areas between them, neither film was apertured on leaving the nip between the rollers. The laminate may be stored on a roll.

Preparation of the Net

The net may be formed in the polymer blend film by separating it from the carrier. The membrane areas of the polymer blend film remain adhered to the polyethylene film. The net had approximately 16 apertures per sq cm each of which had an area of approximately 4 sq mm.

EXAMPLE 2

A laminate formed by a similar method to that described in Example 1 was taken and onto the polymer blend surface was cast a hydrophilic polyurethane foam forming mixture. The mixture was formed by mixing Hypol FHP2002 and Brij 72 in the ratio 1:2.25 and coated via a fish tail die on to the laminate by means of a knife over roller coating head set at a gap of 1 mm. The cast foam was dried by passage through an air circulating oven at a temperature of 50° C. for 5 minutes. The polyethylene film was peeled from the polymer blend film leaving the now apertured polymer blend film adhered to the foam. The material can be used as an absorbent wound dressing in which the apertured polymer blend film forms the contacting layer.

EXAMPLE 3

A polyethylene film-polymer blend film-foam laminate was prepared as described in Example 2. A solution containing 2% by weight of a polyurethane (Estane 5714F) in a mixture of tetrahydrofuran and acetone as solvent was hand sprayed on to the foam surface using an air spray unit and dried by passage through a air circulating oven heated to a temperature of 70° C.

The polyurethane coating was observed to be continuous and had a weight per unit area of 30 grams per square meter.

The polyethylene film was peeled from the polymer blnd film to form the apertures. The film-foam-film laminate could be cut into pieces suitable for use as a absorbent wound dressing and packaged in a bacteria proof pack and sterilized in a conventional manner, for example by gamma irradiation.

EXAMPLE 4

A laminate was formed in a similar manner to that described in Example 1. The net-forming film of the laminate was coated with a foam formed in the following way, polyethylene glycol nonyl phenyl ether (Anterox CO-520, 1 mole) was mixed with an aliphatic isocyanate (Desmodur N 100, 3 moles) and dibutyl tin di laurate as catatlyst in a wide necked jar at a temperature to maintain the components fluid. The reaction product was used to form a foam by mixing with 10% by weight of water. The foaming mixture while fluid was cast onto the net-forming film by the method described in Example 2. The preparation of the foam is described as Example 17 of European Patent Application No. 299122.

EXAMPLE 5

A control wound dressing was manufactured according to the method described in European Patent Specification No. 059049 except that the polyurethane foam was that described in Example 17 of European Patent Specification No. 299122.

The foam was cast onto an Estane net, which itself had been cast onto a polypropylene carrier. A 20 grams per square meter Estane film was then applied to the top surface of the foam and once the foam had cured the carrier was removed.

The thus formed dressing, after sterilization was applied to a partial thickness wound and held in place by adhesive tape for four days.

A dressing as described in Example 4 was placed on a similar partial thickness wound and also held in place by adhesive tape for four days.

The dressing was removed by first removing the adhesive tapes while holding the dressing against the body. The dressings were then removed using a Nene tensile testing machine to measure the force required to break the bond between the dressing and the healing wound surface.

In both cases the dressings were removed cleanly leaving no residues on the healing wound surface. The force required to remove the Control dressing measured 97.68 on the testing machine whereas that required for removing the dressing of the invention was only 40.40.

What is claimed is:

1. An absorbent device which comprises a contoured polymer film having opposed sides, an absorbent layer having a surface thereof attached to one said side and a carrier material attached to the other said side, said carrier material and said contoured polymer film forming a laminate having impressed in said carrier material and contoured polymer film a pattern of raised areas and depressed areas therebetween, said contoured polymer film and said carrier material being attached to each other such that upon separation of one from the other the depressed areas of the contoured polymer film remain adhered to the carrier material leaving behind on said surface of said absorbent layer an apertured film comprising the raised areas of said contoured polymer film, said surface having a plurality of depressions which communicate directly with the apertures in said apertured film, said depressions being free of film.

2. An absorbent device according to claim 1 wherein the carrier has been removed.

3. A device according to claim 1 wherein the apertured contoured polymer film is a net.

4. A device as claimed in claim 1, wherein the apertured film is a net.

5. A device as claimed in claim 1, wherein the contoured polymer film comprises an elastomer.

6. A device as claimed in claim 5, wherein the elastomer is a thermoplastic elastomer.

7. A device as claimed in claim 6, wherein the elastomer comprises a continuous phase of the blend.

8. A device as claimed in claim 7, wherein the elastomer is an ethylene-vinyl acetate copolymer, a polyurethane, or a polyether polyamide.

9. A device as claimed in claim 1, wherein the polymer film is a polymer blend.

10. A device as claimed in claim 9, wherein the polymer blend is a blend of an elastomer and a more rigid polymer.

11. A device as claimed in claim 1, wherein the polymer film comprises a polyolefin.

12. A device as claimed in claim 1 comprising a further layer of a continuous moisture vapor permeable film attached to the surface of the absorbent layer opposed to that attached to the apertured contoured polymer film.

13. A device as claimed in claim 12, wherein the further layer has moisture vapor transmission rate in a range of from about 300 gsm to about 500 gsm.

14. A device as claimed in claim 13, wherein the moisture vapor permeable film is made of an elastomeric material.

15. A device as claimed in claim 14, wherein the elastomeric material comprises a polyurethane, an ethylene-vinyl acetate copolymer, or a polyether-polyester.

16. A device as claimed in claim 1, wherein the absorbent layer is a foam.

17. A device as claimed in claim 16, wherein the foam is a polyurethane foam.

18. A device as claimed in claim 17, wherein the polyurethane foam is a hydrophilic polyurethane foam.

19. A device as claimed in claim 1 having a moisture vapor transmission rate in a range from about 300 gsm to about 2,000 gsm.

20. A device as claimed in claim 1 configured as a wound dressing, sanitary towel, or a diaper.

* * * * *